United States Patent
Gil

(10) Patent No.: US 12,138,147 B1
(45) Date of Patent: Nov. 12, 2024

(54) URINARY INCONTINENCE MITIGATOR, "THE MITIGATOR"

(71) Applicant: Abel Antonio Gil, Miami, FL (US)

(72) Inventor: Abel Antonio Gil, Miami, FL (US)

(*) Notice: Subject to any disclaimer, the term of this patent is extended or adjusted under 35 U.S.C. 154(b) by 0 days.

(21) Appl. No.: 18/345,006

(22) Filed: Jun. 30, 2023

Related U.S. Application Data

(60) Provisional application No. 63/577,385, filed on Apr. 20, 2023.

(51) Int. Cl.
*A61F 2/00* (2006.01)

(52) U.S. Cl.
CPC .................. *A61F 2/0004* (2013.01)

(58) Field of Classification Search
CPC .................. A61F 2/0004; A61F 2/0009
See application file for complete search history.

(56) References Cited

U.S. PATENT DOCUMENTS

| | | | | |
|---|---|---|---|---|
| 5,334,175 A | * | 8/1994 | Conway | B29C 41/22 604/347 |
| 5,380,312 A | * | 1/1995 | Goulter | A61F 5/453 604/352 |
| 5,800,339 A | * | 9/1998 | Salama | A61F 2/0009 128/DIG. 25 |
| 6,679,867 B2 | * | 1/2004 | Miskie | A61F 5/453 604/323 |
| 2019/0021899 A1 | * | 1/2019 | Vlet | A61F 2/0009 |

* cited by examiner

*Primary Examiner* — Steven O Douglas
(74) *Attorney, Agent, or Firm* — Talem IP Law, LLP

(57) ABSTRACT

A urinary incontinence device includes a cylindric section having a first end with a necklace, the necklace structured to hold in place at a base of a penis; an oval section extending from a second end of the cylindric section; and an internal valve at the second end of the cylindric section. All components are integrated together in one single, small, and easy "fit-and-go" device; keeps all components in one small area of the pelvic zone and does not need to alter the normal clothing dress.

7 Claims, 4 Drawing Sheets

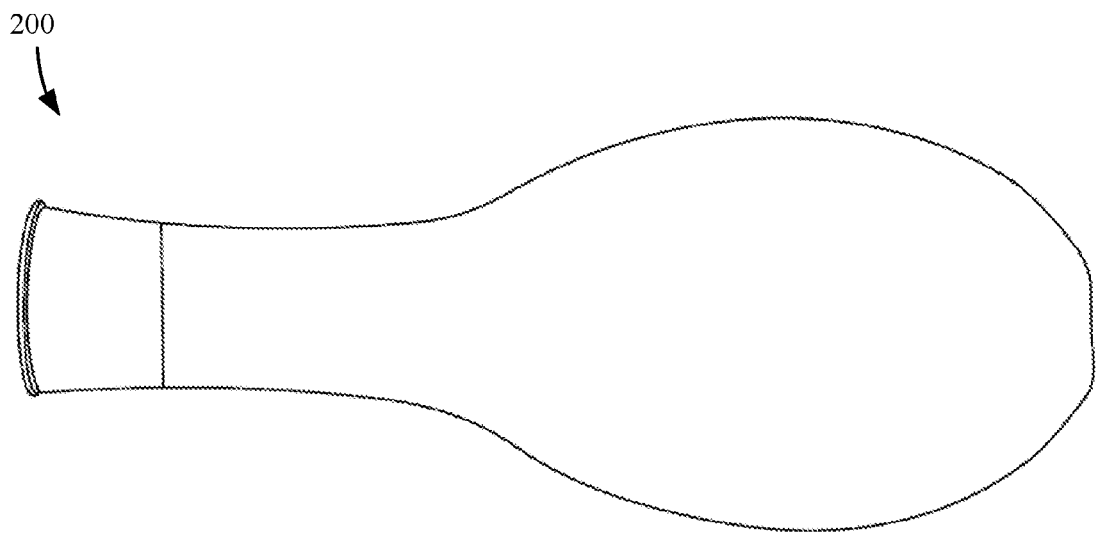
FIG. 2A
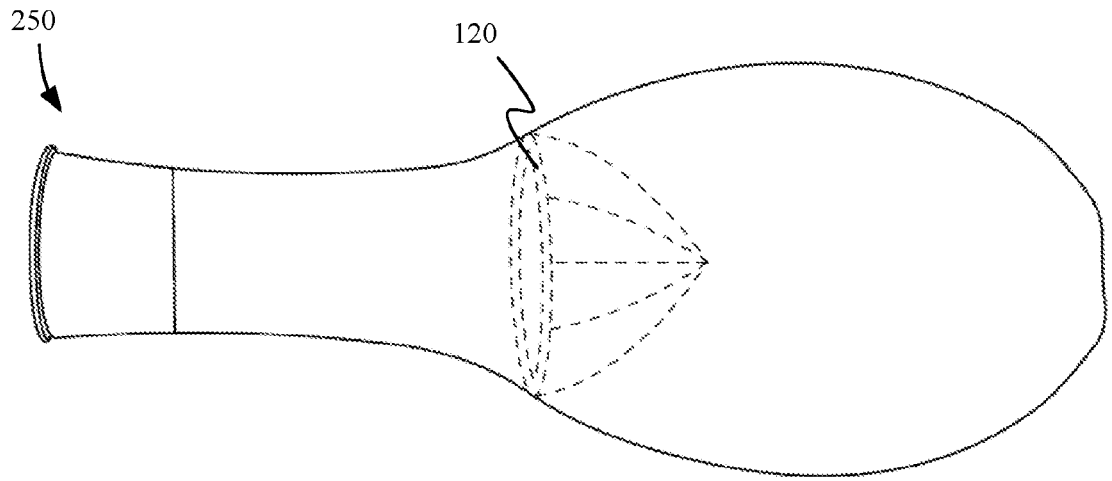
FIG. 2B
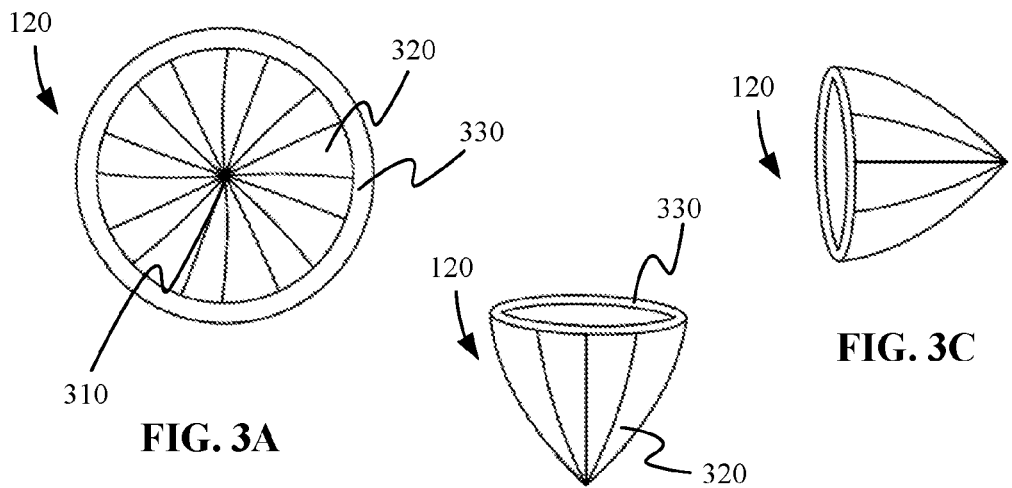
FIG. 3A
FIG. 3B
FIG. 3C

URINARY INCONTINENCE MITIGATOR, "THE MITIGATOR"

BACKGROUND OF THE INVENTION

In the world, about sixty million men are suffering from urinary incontinence, ("Consultor salud, Sep. 20, 2021 "200 millones de personas sufren de incontinencia urinaria en el mundo. Abece de la incontinencia"), caused by personal health conditions or due to secondary effects of prostatic surgeries, producing an unhygienic and emotional condition, that adversely affects the quality of life for many men; to minimize this problem, there are in the market some products that partially helps, but some of them do not keep entirety dry and others make the patient feels like wearing a prothesis, or a sophisticated apparatus that psychologic make the patient feels more miserable and disability, some of these products are, adults pampers, sanitary pads, incontinence clamps, rubber condom with hose and receptor, or sophisticated underwear with rubber condom and receptor. In the effort to find a more efficient, discrete, and less traumatic solution, I have found a new way to face this problem, from the adaptation and modification of the design of existing products intended for other purposes.

BRIEF SUMMARY OF THE INVENTION

This invention is a sanitary and practical device created to dismiss the uncomfortable and anti-hygienic conditions caused by urinary incontinence on men and to provide a manner to face this health problem in a more natural, discrete, and less traumatic way. It is in some manner a sensual way to face it, and it gives the sensation of being an extension of its own bladder, which can be voluntary controlled, it is a "fit and go devise". It is not a cure for such conditions but a way to face it while lasts.

This device will meet with the following objectives:
- a: To provide a better alternative to the use of a catheter, adult pampers, pads, incontinence clamps, rubber condoms or uncomfortable underwear for incontinent men.
- b: To provide a practical solution to pants being soaked due to continuous urine leaks by incontinent men.
- c: Avoid the permanent contact of skin with the expelled urine that may be unhygienic and a health problem, and an uncomfortable situation.
- d: To find a less stressful and more pleasurable way to face the incontinence inconvenient.

BRIEF DESCRIPTION OF THE DRAWINGS

FIG. 2A shows a plain version of the mitigator with non-internal valve.

FIG. 2B shows a plain version of the mitigator with internal valve.

FIG. 3A shows a back view of the internal valve.

FIG. 3B shows a side view of the internal valve.

FIG. 3C shows a side view of the internal valve.

DETAILED DESCRIPTION OF THE INVENTION

The URINARY INCONTINENCE MITIGATOR, "THE MITIGATOR" is one piece device, made by latex and rubber, equally flexible, thin and transparent as a condom, (texture must be same of a condom, and transparency is required to be able to observe through at all times), cylindric on the section that is adjustable to the man's member and more oval or round at the end, like a balloon, with a self-opening and closing valve inside it, (like an sphincter) where the cylindric and oval sections meets, to allow urine to go out, and to prevent it from returning to the penis once it is collected by the oval section of this device, also this internal valve fits the man's glans and it is fastened with a latex ring around the glan's neck to provide support once the collector is full (see FIGS. 1A, 1D, 2B, and 3A-3C for internal valve).

Figure 1A:
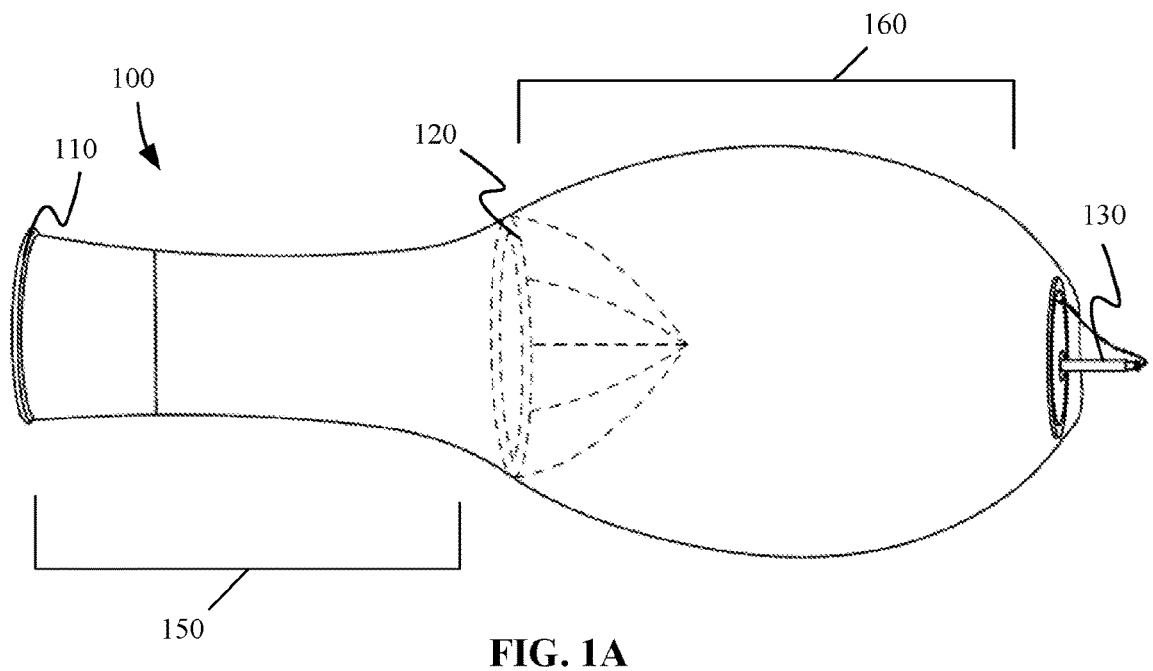
FIG. 1A shows a basic version of the mitigator with its design and components (necklace, internal valve, and external valve).
Figure 1B:
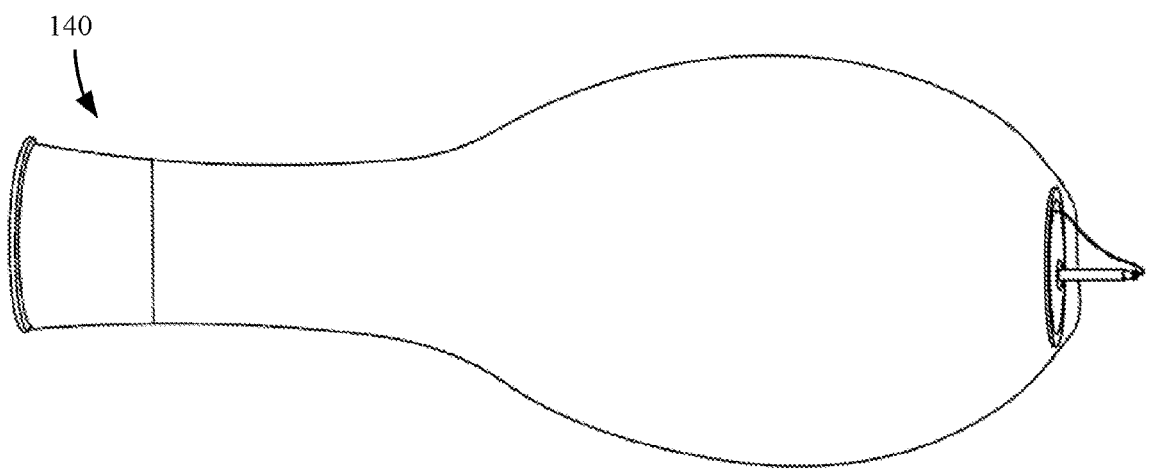
FIG. 1B shows a basic version of the mitigator with no internal valve.
Figure 1C:
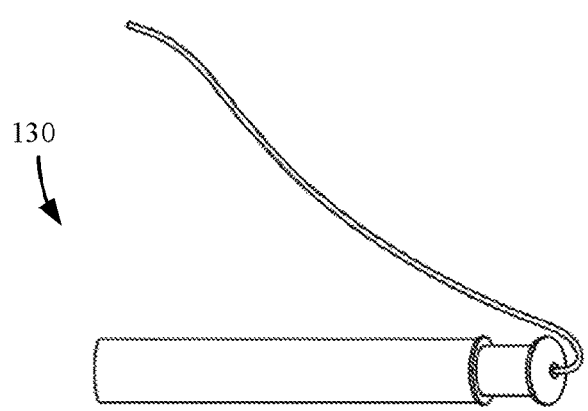
FIG. 1C shows details of the external valve, (enlarged view).
Figure 1D:
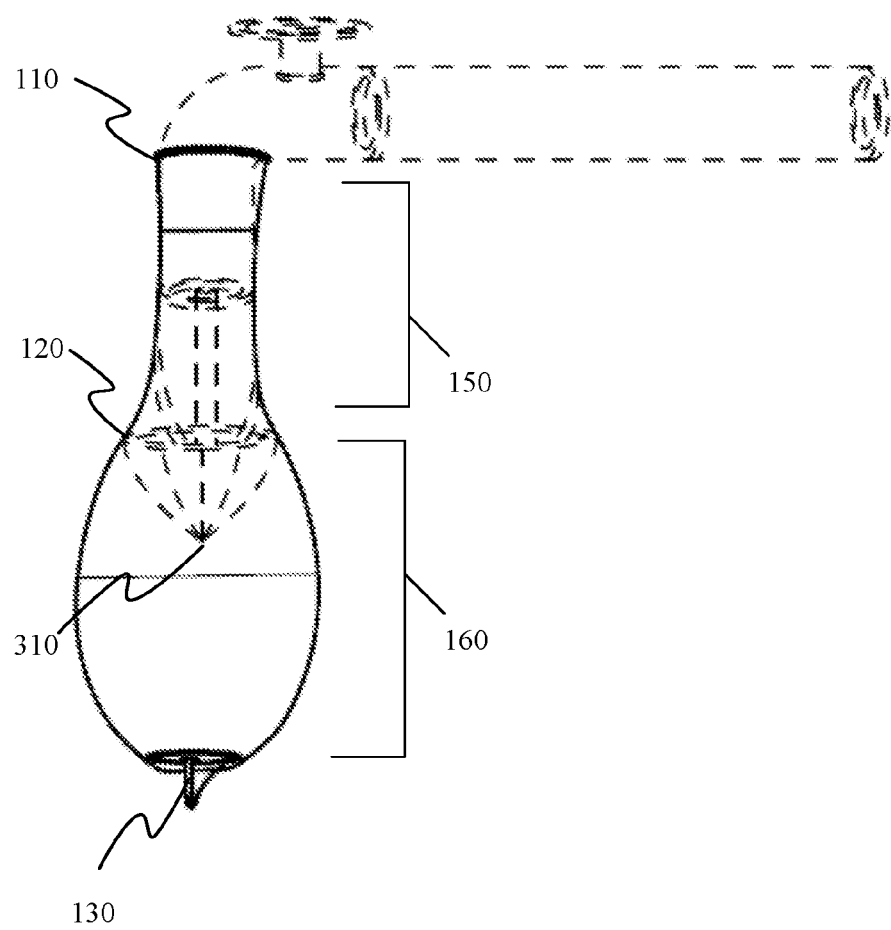
FIG. 1D shows a symbolic use of the invention, basic & plain versions, (reduced view).

FIG. 1A shows a basic version of the mitigator 100 with its design and components (necklace 110, internal valve 120, and external valve 130); FIG. 1B shows a basic version of the mitigator with no internal valve (mitigator 140); FIG. 1C shows details of the external valve 130, (enlarged view); and FIG. 1D shows a symbolic use of the invention, basic & plain versions, (reduced view). Referring to FIG. 1A, the mitigator 100 has a cylindric section 150 and an oval section 160. Internal valve 120 is inside the mitigator 100 where the cylindric section 150 and the oval section 160 meet. FIGS. 3A-3C show back and side views of the internal valve 120. Internal valve 120 is formed of a ring 330 that attaches the self-opening pieces 320 to the end of the cylindric section 150. With reference to FIG. 1D and FIGS. 3A-3C, fluid is able to be released from the cylindric section 150 to the oval section 160 through a hole 310 that expands as a result of the self-opening pieces 320 separating due to the secreted urine.

The cylindric section 150 comes rolled on itself to facilitate an easy attachment to the male member by unrolling manually to fit it and is made of a thin but strong and flexible latex sheet to assure an adequate and firm attachment to the male member, without compressing too much but enough to stay in position and hold any considerable amount of secreted urine; the cylindric section 150 is long enough, as a regular condom, and ends with a rubber type ring or necklace 110 on the tip or border to better hold the device, soft and flexible enough to prevent compressing too much. In the oval section 160 the device ends with a thicker manually opening and closing valve 130 made of the same latex material, to empty the urine once collected by the mitigator (see FIGS. 1A-1D for external valve). Available in small, medium, and large presentations for a better fitting on different men's sizes, as well as in multiple varieties of colors; flavored or simple; dry, lubricated or powdered; this basic version (see FIGS. 1A, 1B, and 1D) of the mitigator, also come on its plain (see FIGS. 2A and 2B) and extended versions (see FIGS. 4A and 4B).

FIG. 2A shows a plain version of the mitigator 200 with non-internal valve and FIG. 2B shows a plain version of the mitigator 250 with internal valve 120. For short term and quick use, there is a simple or plain version of this device (e.g., mitigator 200, 250) without an external valve at the tip and with or without an internal valve 120 or sphincter. This version allows the patient to have at hand a small and practical protector that can be carried out all the time to face any emergency, and at a more economical cost (see FIGS. 2A and 2B).

Figures 4A, 4B:
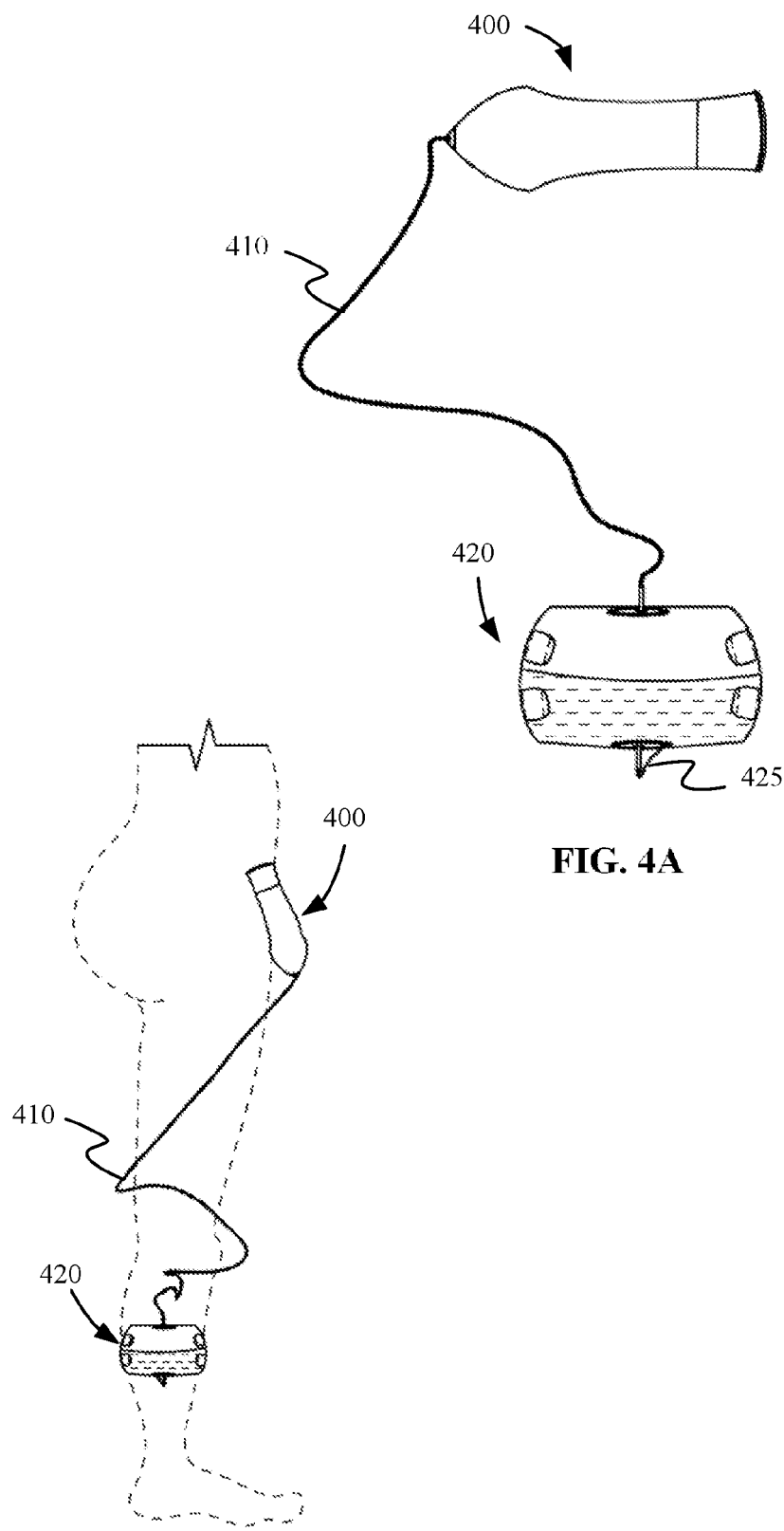
FIG. 4A shows an extended version of the mitigator.
FIG. 4B shows a sample use of extended version of the mitigator.

Also, referring to FIGS. 4A and 4B, this device is available in an extended version consisting of two sections sealed together: The first section 400 is the cylindric part, ending on the tip with no urine holder but with a prolonged, thin, rubber or latex hose 410 instead of the external valve at the tip; this thin latex hose 410 will be long enough to reach the leg of a man where an ending urine receptor 420 will be integrated. The receptor 420 will end on the external valve 425 on the bottom that can be manually opened and closed to empty the urine as needed and is attached to the leg by two strips with VELCRO. This Extended Version has the advantages over the basic version, which can be used for more time without emptying it, and one device can be used for more hours during the day. It will be more sophisticated, with more components and being more expensive (see FIGS. 4A and 4B).

Packaging Presentation

The URINARY INCONTINENCE MITIGATOR, "the mitigator" will come in individual presentations for each version (Basic, Plain, Extended) to sell each piece separately in packs of 3 to 36, or in a family pack containing all three versions of it, with packs of 3 (one of each version) to 7 (3 Basic, 3 Plain, 1 Extended Version).

Suggested measurements for the mitigator include 3-5 cm diameter for the necklace 110, 7-16 cm length for the cylindric part 150, 4-9 cm length for the oval part 160, 3 cm length (with lid diameter of 0.4 cm and outer diameter of 0.75 cm) for the external valve 130, and a 3.5-5 cm diameter of the ring 330 of the internal valve 120 and 3-6 cm length of internal valve 120.

The invention claimed is:

1. A urinary incontinence device, comprising:
   a cylindric section having a first end with a necklace, the necklace structured as a ring to hold in place at a base of a penis;
   an oval section extending from a second end of the cylindric section; and
   an internal valve at the second end of the cylindric section, wherein the internal valve comprises:
   a ring that attaches within the second end of the cylindric section; and
   self-opening pieces extending from the ring and into the oval section to meet at their tips when in a closed position, the self-opening pieces structured to separate to form a hole where they meet at their tips due to secreted urine.

2. The urinary incontinence device of claim 1, wherein the necklace is formed of rubber.

3. The urinary incontinence device of claim 1, further comprising an external valve at an end of the oval section that releases urine collected in the oval section.

4. The urinary incontinence device of claim 3, wherein the external valve is a manually operated valve.

5. The urinary incontinence device of claim 1, wherein components are integrated in one single device.

6. The urinary incontinence device of claim 1, wherein the urinary incontinence device is made of latex.

7. The urinary incontinence device of claim 1, wherein the cylindric section and the oval section together form a balloon shape.

* * * * *